United States Patent [19]

Luks et al.

[11] Patent Number: 4,766,558
[45] Date of Patent: Aug. 23, 1988

[54] METHOD OF CALCULATING MINIMUM MISCIBILITY PRESSURE

[75] Inventors: Kraemer D. Luks; Edward A. Turek; Lee E. Baker, all of Tulsa, Okla.

[73] Assignee: Amoco Corporation, Chicago, Ill.

[21] Appl. No.: 842,506

[22] Filed: Mar. 21, 1986

[51] Int. Cl.⁴ .................... G06F 15/46; E21B 43/16
[52] U.S. Cl. ............................ 364/558; 55/16; 73/61.1 R; 166/273; 166/274; 364/502
[58] Field of Search ............ 364/500, 502, 558; 166/273, 274; 62/17, 20, 24; 73/19, 61 R, 61.1 R; 55/16, 68

[56] References Cited

U.S. PATENT DOCUMENTS

| | | | |
|---|---|---|---|
| 4,092,847 | 6/1978 | Lynch et al. | 364/502 |
| 4,136,738 | 1/1979 | Haynes, Jr. et al. | 166/273 |
| 4,318,723 | 3/1982 | Holmes et al. | 62/24 |
| 4,444,576 | 4/1984 | Ryan et al. | 62/20 |
| 4,455,860 | 6/1984 | Cullick et al. | 73/61.1 R |
| 4,459,142 | 7/1984 | Goddin, Jr. | 62/17 |
| 4,466,946 | 8/1984 | Goddin, Jr. et al. | 62/24 |
| 4,467,868 | 8/1984 | Adamache | 166/273 |
| 4,509,596 | 4/1985 | Emery | 166/273 |
| 4,513,821 | 4/1985 | Shu | 166/273 |
| 4,529,411 | 7/1985 | Goddin, Jr. et al. | 62/44 |
| 4,557,330 | 12/1985 | Russell et al. | 166/273 |
| 4,558,740 | 12/1985 | Yellig, Jr. | 166/274 |
| 4,617,996 | 10/1986 | Shu | 166/273 |
| 4,627,273 | 12/1986 | Christiansen et al. | 73/61.1 R |

Primary Examiner—Parshotam S. Lall
Assistant Examiner—Kevin J. Teska
Attorney, Agent, or Firm—L. Wayne White; Scott H. Brown

[57] ABSTRACT

A method is disclosed for determining the minimum miscibility pressure of a three (3) or more component fluid system consisting of an in-place fluid and an injected fluid, such as a mixture of liquid and gaseous hydrocarbons and another gas, such as $CO_2$ or nitrogen. For a given pressure, the concentration of the first fluid is varied until a multiphase fluid state is indicated. The coexisting equilibrium phase compositions are calculated to determine a tieline which is translated geometrically retaining the direction of its slope to estimate a new tieline which attempts to be coincident with the second fluid's composition. The method above is repeated utilizing an increased pressure if the new tieline is coincident with a second fluid's composition and utilizing a decreased pressure if a coincident tieline does not exist, until a boundary pressure is achieved which represents the minimum miscibility pressure.

9 Claims, 4 Drawing Sheets

METHOD OF CALCULATING MINIMUM MISCIBILITY PRESSURE

BACKGROUND OF THE INVENTION

1. Field of the Invention

The present invention relates to a method of calculating a minimum miscibility pressure and, more particularly, to such a method that utilizes parallel translation of coexisting equilibrium phase compositions to quickly determine the minimum miscibility pressure.

2. Setting of the Invention

For enhanced oil recovery processes involving injection of an inert gas, such as $CO_2$ or nitrogen, miscibility with the in-place fluids in the formation can be developed through one of two multiple-contact mechanisms at pressures where first-contact phase equilibrium measurements show two-phase behavior. The two multiple-contact mechanisms are a leading edge miscibility or vaporizing mechanism, and a trailing edge miscibility or a condensing mechanism. To properly model such processes utilizing a programmable digital computer, with an equation-of-state computer program, fluid descriptions consistent with multiple-contact miscibility development are utilized. One measure of this consistency is an agreement between the minimum miscibility pressure determined from slim-tube displacements and the thermodynamic minimum miscibility pressure calculated using a programmable digital computer. Publications have previously described miscible processes using triangular compositional diagrams for the purpose of the conceptual analysis of determining the thermodynamic minimum miscibility pressure. After the minimum miscibility pressure has been determined, it is compared to laboratory results, such as the slim-tube displacements. In the equation-of-state descriptions of the fluids, usually properties of the $C_7+$ components of the in-place oil, are adjusted to bring the descriptions into agreement. There are two common idealizations of the way in which the two-phase gas and liquid system achieves miscibility through multiple contacts. In the vaporizing mechanism, fresh or original liquid phase contacts the vapor phase whose composition is altered by repeated equilibration with the liquid. In the condensing mechanism, the composition of the liquid phase is altered by equilibration with the fresh vapor phase. The definition of thermodynamic miscibility pressure is that pressure at a fixed temperature, above which miscibility occurs for a given feed, i.e., a liquid or an oil, and the pressurizing gas solely through the multiple contact equilibrium process. The computation of this pressure is dependent upon the mechanism involved; the thermodynamic minimum miscibility pressure is assumed to be the lower of two determined bounds.

Previous methods to determine the minimum miscibility pressure have used equations of state to determine the vapor-liquid equilibrium tieline behavior combined with a strategy to locate the limiting or critical coincident tieline. A pressure is chosen for a given temperature below the thermodynamic minimum miscibility pressure. An iterative procedure is invoked to locate the coincident tieline at this pressure, usually a stepping procedure that locates to some acceptable degree of convergence the coincident tieline. The pressure is incremented upwards to locate the thermodynamic minimum miscibility pressure, taking advantage through extrapolation of the fact that the equilibrium ratio values will approach unity as the limiting coincident tieline is approached. The problem encountered in the past has been that the stepping procedure is inherently slow to approach the coincident tieline, requiring many steps. It is slowest when closest to the coincident tieline, and some judgment must be exercised by the user as to what constitutes the satisfactory location or convergence. It has become apparent to those skilled in the art that a more accurate method of determining the thermodynamic minimum miscibility pressure utilizing a programmable digital computer is needed; as well, there is a need for such a method that is more computationally efficient than those previously utilized.

SUMMARY OF THE INVENTION

A method is disclosed to determine the minimum miscibility pressure of a three (3) or more component fluid system encountered during the displacement of an in-place fluid with an injected fluid. The method has been developed to overcome the foregoing deficiencies and to meet the above-described needs. In the method, for a given initial pressure of the fluid, the concentration of the injected fluid is varied until a multiphase fluid state is indicated. Thereafter, the coexisting equilibrium phase compositions are calculated for the multiphase fluid to define a tieline. The tieline is parallel translated, retaining the direction of its slope, to estimate a new tieline that is coincident with the in-place fluid's composition for a vaporizing mechanism or the injected fluid's composition for a condensing mechanism, the midpoint of which locates a multiphase fluid state. After convergence is achieved, the previous steps are reiterated using an increased pressure if a coincident tieline was located and utilizing a decreased pressure if a coincident tieline could not be located, until a boundary pressure is achieved representing the minimum miscibility pressure.

The above-described method is not only more accurate than previously described methods but is also more computationally efficient, therefore utilizing less computer time, thereby saving time and money for the operator.

DETAILED DESCRIPTION OF THE DRAWINGS

DETAILED DESCRIPTION OF THE PREFERRED EMBODMENTS

A method is disclosed for determining the minimum miscibility pressure of a three (3) or more component fluid, such as a fluid including liquid and gaseous hydrocarbons such as those in-place within an oil-bearing reservoir, and a fluid including $CO_2$, nitrogen, liquid and gaseous hydrocarbons which may be injected. For an initial pressure, a concentration of the injected fluid is varied upwards or downwards until a multiphase fluid state is indicated. The coexisting equilibrium phase compositions are calculated using an equation of state algorithm to define a tieline. Thereafter, the tieline is parallel translated, retaining the direction of its slope to estimate a new tieline that is coincident with the in-place fluid's composition for a vaporizing mechanism or the injected fluid's composition for a condensing mechanism. The midpoint of the new tieline serves as the multiphase fluid state. Following convergence, the above steps are repeated utilizing an increased pressure of the fluid if a coincident tieline is located and utilizing a decreased pressure if no coincident tieline is located, until a boundary pressure is achieved representing the miscibility pressure.

Figure 1:
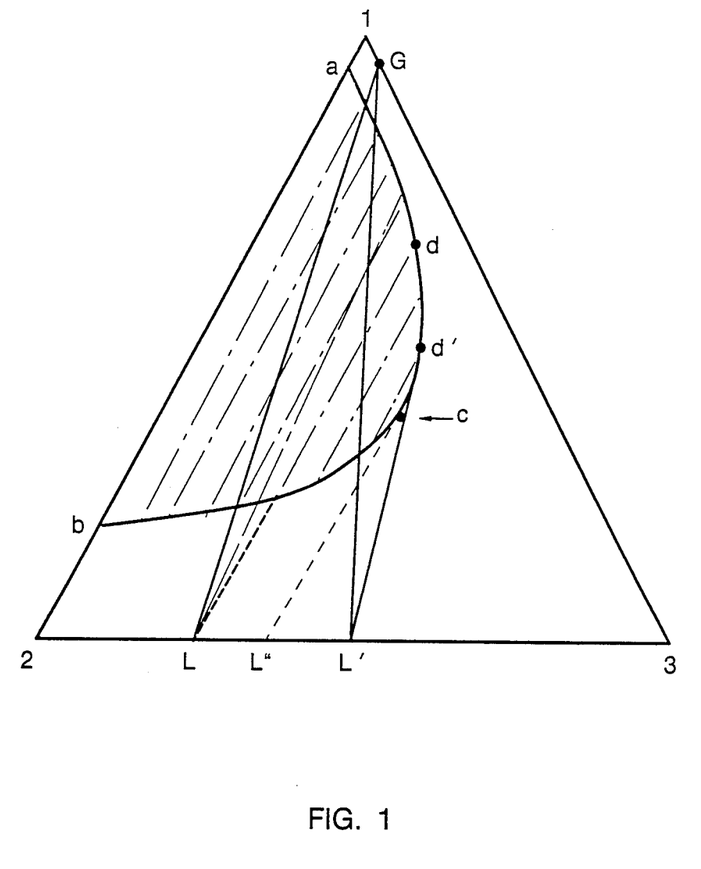
FIG. 1 is a ternary compositional diagram at some fixed temperature and pressure where the initial gas stream is denoted by G, and possible initial liquid streams are labeled L, L', L'', and c is the two-phase critical point.

The method of the present invention can be represented as an algorithm for use with a programmable digital computer for calculating the thermodynamic minimum miscibility pressure consistent with an equation of state fluid description. The algorithm can determine the miscibility by both condensing and vaporizing mechanisms and encompasses the use of mixtures of three or more pure components as well as reservoir oil-$CO_2$ systems, for example. To better understand the present invention, a brief description of the prior art methods are described with respect to FIG. 1. FIG. 1 illustrates a ternary gas and liquid system at a fixed temperature and pressure. First consider the vaporizing mechanism of two initial gas and liquid streams, G and L, respectively. The vaporphase composition is altered by multiple contacting, its composition moving from G to the saturated vapor curve $\overline{ac}$, eventually approaching the composition d in asymptotic fashion. No further alteration of the gas phase occurs since the tieline through d is coincident with the composition L; the conclusion is that the miscibility cannot be achieved for the system G and L by thermodynamic multiple contacting alone at this temperature and pressure.

If the two initial streams had been G and L', a single phase or a miscible state would have eventually occurred. The gas phase would have moved along the curve $\overline{ac}$ until the line contacting the gas phase with L' would no longer pass through the two-phase region. This limiting gas phase composition associated with L' is denoted by d'. At this temperature and pressure, miscibility is achieved for the system G+L'.

The limiting initial liquid stream composition for achieving miscibility, given G, is denoted L", and can be located by extending a tangent line to the twophase region at the critical point c. For an initial mixture of G+L", this pressure at this temperature is the thermodynamic minimum miscibility pressure for the vaporizing mechanism. If one assumes that the extent of the two-phase region shrinks with increasing pressure, one can envision the eventual intersection of the tangent line to the vapor-liquid critical point at L; that is, the thermodynamic minimum miscibility pressure for L is greater than that for L" and L' at this temperature for the vaporizing mechanism.

One can make similar observations about the condensing mechanism, concluding that all three (3) systems, G+L, L' and L" are thermodynamically immiscible by the condensing mechanism at this pressure, as there is a tieline whose extension intersects G. Consequently, for the systems G+L or L' or L", the thermodynamic minimum miscibility pressure is determined by the vaporizing mechanism, as the condensing mechanism requires a considerably higher pressure at this temperature to be miscible. The pressure denoting the bound between the miscible and immiscible state for the condensing mechanism will be that one which has a tangent line to the critical point c intersecting G. Variation in the location of G causes a change in the value of the thermodynamic minimum miscibility pressure as determined by the condensing mecharism, in the same manner that it is altered for the vaporizing mechanism by a change in the location of the liquid composition L.

The preceding illustration suggests a methodology, cast in geometrical terms, for the computation of the thermodynamic minimum miscibility pressure, which the inventors hereof have utilized for the present invention. Specifically, for a given mechanism, a point below the thermodynamic minimum miscibility pressure occurs if there is a tieline, connecting the equilibrium liquid and vapor compositions, collinear or "coincident" with the original unaltered feed. The pressure at which the length of this coincident tieline goes to zero is the pressure at which there is a tangent to the critical point collinear with the original unaltered feed. The lower of the two thermodynamic miscibility boundary pressures for the vaporizing and condensing mechanisms is generally assumed to be the appropriate computed thermodynamic minimum miscibility pressure.

Figure 2:
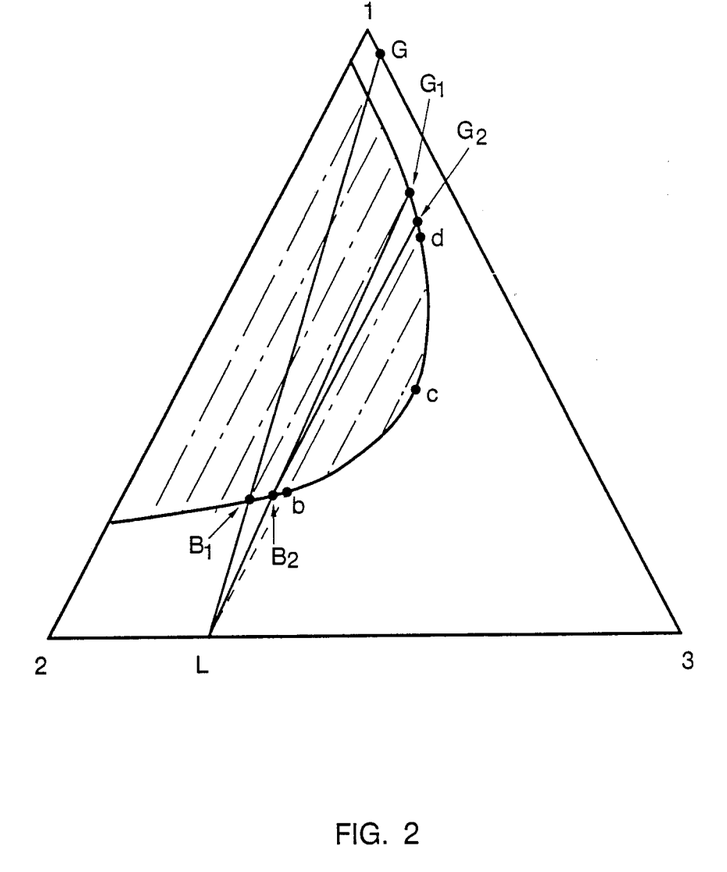
FIG. 2 is an illustration of a coincident tieline being located by a stepping procedure for a vaporizing mechanism.

Previous investigators have used equations of state to determine the vapor-liquid equilibrium tieline behavior combined with a strategy to locate the limiting or critical coincident tieline. As previously discussed, prior methods initially chose a pressure for the given temperature below the thermodynamic minimum miscibility pressure. An iterative procedure was invoked to locate the coincident tieline at this pressure, usually a stepping procedure, for example the type shown in FIG. 2 for a vaporizing mechanism. In FIG. 2 streams G and L are mixed, at a bubblepoint state $B_1$ with which $G_1$ is the equilibrium vapor. In turn, $G_1$ is mixed with L to create $B_2$ and so forth. A coincident tieline $\overline{bd}$ is approached asymptoticaly, where $$b = \lim_{n \to \infty} B_n \text{ and } d = \lim_{n \to \infty} G_n.$$

This stepping procedure locates to some acceptable degree of convergence the coincident tieline. The methods described previously increment the pressure upwards to locate the thermodynamic minimum miscibility pressure, taking advantage through extrapolation of the fact that the values of the equilibrium ratio $K_i$ where $K_i = Y_i/X_i$ where $Y_i$ is the composition of the fluid species i in fluid d and $X_i$ is the composition of the species i in fluid b will approach unity as the limiting coincident tieline is approached.

There are at least three (3) differences in the method of the present invention and those set forth previously. First of all, an analysis is used to examine the single-phase stability of mixtures prior to performing a flash calculation, i.e., the calculation of the coexisting equilibrium phase compositions that define a tieline. Secondly, a robust algorithm utilizing parallel displacement or translation is used, possibly in concert with the traditional stepping procedure outlined above, to locate the coincident tieline.

Preferably, when the vaporizing mechanism is chosen and prior to the parallel displacement of translation step, a stepping procedure is chosen which comprises:

(i) for a given concentration of a first fluid (G) and a second fluid (L) determining an initial bubblepoint state $B_n$ where $G_n$ is the equilibrium vapor;

(ii) determining a new bubblepoint state $B_n+1$ from a mixture of L and $G_n$; and (iii) repeating steps i and ii to approach a coincident tieline $\overline{bd}$ where $$b = \lim_{n \to \infty} B_n$$

$$d = \lim_{n \to \infty} G_n$$

Also prefered, when the condensing mechanism is chosen and prior to the parallel displacement or translation step, a stepping procedure is chosen which comprises:

(i) for a given concentration of a first fluid (G) and a second fluid (L) determining an initial dewpoint state $D_n$ wherein $L_n$ is the equilibrium liquid;

(ii) determining a new dewpoint state $D_n+1$ from a mixture of $L_n$ and G; and (iii) repeating steps i and ii to approach a coincident tieline $\overline{bd}$ wherein $$b = \lim_{n \to \infty} L_n$$

$$d = \lim_{n \to \infty} D_n.$$

Finally a half-interval search is used to locate the thermodynamic minimum miscibility pressure; this approach requires execution of a search for a coincident tieline typically as often at pressures greater than the thermodynamic miscibility pressure as at pressures below the thermodynamic miscibility pressures. Above the thermodynamic miscibility pressure, any such search to locate a coincident tieline is obviously futile. The benefits of the utilization of one or more of these improvements over the previous methods provide a significant saving of the computer time required to compute a thermodynamic miscibility pressure for a given mechanism, either vaporizing or condensing. The parallel displacement algorithm appears as well as to enhance the precision with which the coincident tieline is located.

In order to identify a coincident tieline, one must first locate the two-phase region. For example, in FIG. 3, a point in the two-phase region along the line $\overline{LG}$ is found and then a flash calculation is performed, i.e, the calculation of the coexisting equilibrium phase compositions for the multiphase fluid that defines a tieline. If $B_2$ is the single-phase region, the result is a trivial solution in which the two phases are identical in properties. It has been shown in the past that a single phase is unstable, i.e., more than one fluid phase exists, if an appropriate stationary point can be found. This is the case for a mixture composition $B_1'$. Finding a stationary point is equivalent to demonstrating that a tangent plane to a Gibbs energy surface spanning the range of possible fluid compositions for the system of interest intersects the surface elsewhere than at the point(s) of tangency. In the context of the present discussion, the existence of the stationary point dictates the performance of a flash calculation.

Figure 3:
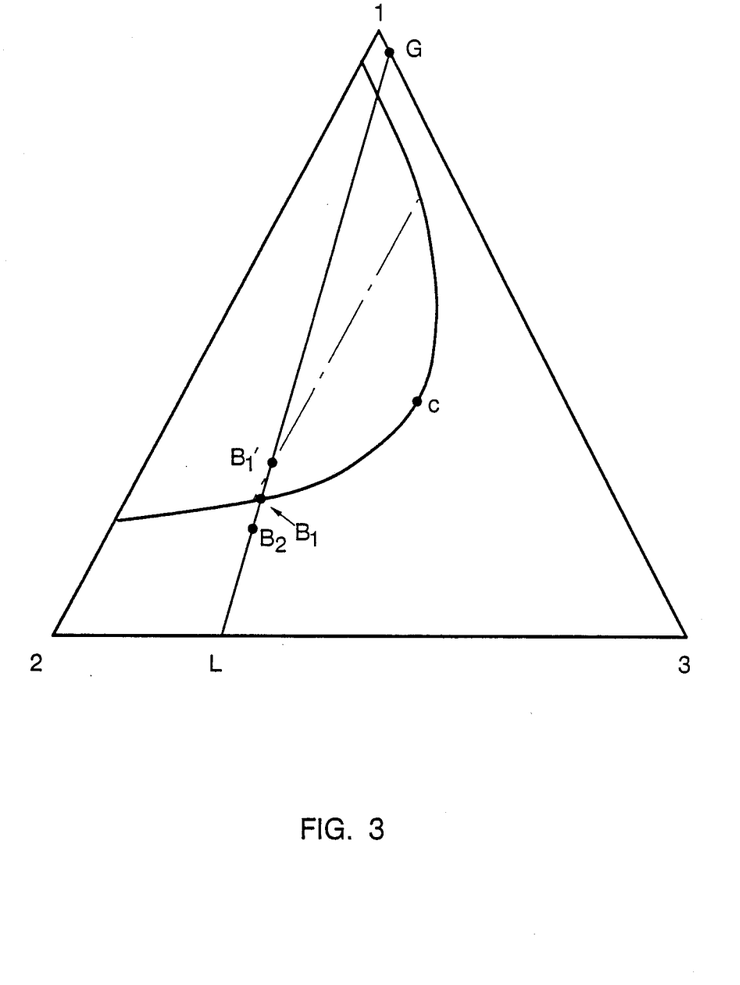
FIG. 3 is an illustration of a one-phase state ($B_2$) and a two-phase state ($B_1'$), at which a flash calculation is performed during a determination of the TMMP by the present invention.

At any pressure at which a coincident tieline is sought, it is advantageous to perform a stationary point search at points such as $B_2$ and $B_1'$ to determine whether a flash calculation should follow. The computational effort required to recognize a trivial solution, i.e., a failure to find a good two-phase solution, at a point $B_2$, is much greater, three (3) to ten (10) times greater in some circumstances, than that required to investigate the likely stationary points. It has been shown that the equations for the location of a stationary point are readily adaptable to a first order successive substitution convergence routine. Further, it has been found that the institution of a Newton's (second order) convergence routine after a few initial successive substitution convergence steps can significantly reduce the computer time required to locate the stationary point or its absence.

Figure 4:
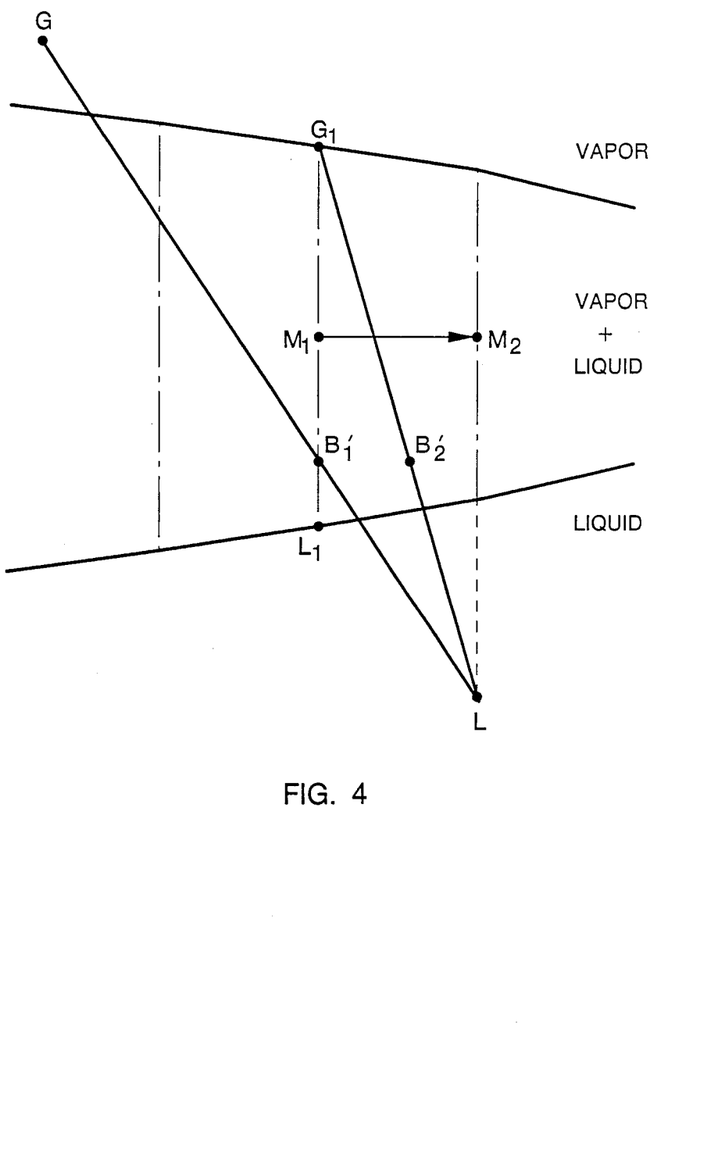
FIG. 4 is a schematic illustration of a single step of the parallel displacement algorithm of the present invention for a vaporizing mechanism.

The stepping procedure as shown in FIG. 2 is inherently slow to approach the coincident tieline and requires many steps, while the use of the parallel displacement algorithm as of the present invention can greatly shorten the time required to locate the coincident tieline, typically with increased precision. In any local region of compositional space, with temperature and pressure fixed, it is assumed that the tielines connecting the vapor and liquid surfaces are reasonably parallel. The implication of this is that, given a tieline from a flash calculation reasonably close to the coincident tieline, one can readily locate the coincident tieline as it must be nearly parallel to the previous tieline; the coincident tieline passes by extension through the composition of that fluid which is unaltered according to the mechanism chosen. FIG. 4 demonstrates this relation, and suggests that one can be assured of staying in the two-phase region by choosing the next flash calculation point to be an estimate of the center of a new tieline that has been parallel displaced. A flash calculation is performed at $B_1'$ yielding a tieline connecting $G_1$ and $L_1$. The midpoint of the tieline is $M_1$. Geometry quickly permits locating $M_2$ which is on the line extending from L parallel to $\overline{L_1G_1}$, and the line $\overline{M_1M_2}$ is perpendicular to $\overline{L_1G_1}$. If all the tielines are exactly parallel, the coincident tieline would be analytically located in one step. However, this is not often the case, so a flash calculation is performed at $M_2$ yielding $G_2$ and $L_2$ (not shown) which can be used as before to locate $M_3$ and so on. For the case of nearly parallel tielines, the tieline $\overline{G_2L_2}$ resulting from a flash calculation of $M_2$ should be much closer to the coincident tieline than the tieline resulting from the flash calculation mixtures of $G_1+L$ (say $B_2'$). The convergence algorithm utilized is more robust and powerful the closer the tielines are to the coincident tieline. This is in direct contrast to the stepping procedure utilized in the past. On the other hand, given the existence of a coincident tieline at the pressure of interest, parallel displacement from large distances in compositional space can sometimes place the point $M_2$ outside the two-phase region, perhaps even outside the physical compositional space ($0 < X_i < 1$, $i = 1, -n$). A judicious use of this algorithm, often times beneficial, is to utilize a number of iterations of the previously described stepping procedure prior to the parallel displacement algorithm described above. Such iterations can number between 1-5 for example. One can use the perpendicular distance from the unaltered composition, L in FIG. 4 in the case of a vaporizing mechanism, to a tieline extension as a criterion for determining the closeness to the coincident tieline.

As previously described, prior art methods have sought to stay below the thermodynamic minimum miscibility pressure when trying to determine the miscibility pressure, the rationale being to follow the disappearance of the coincident tieline in some way. Actually, it often takes less computer time using the stepping procedure described above to determine that there is no coincident tieline (P>TMMP) than to locate one (P<TMMP). As shown earlier with regards to FIG. 1, the determination of a vaporizing mechanism with streams G and L' will eventually lead to a line connecting d' and L' between which there is no two-phase region. This can be verified by applying Gibbs energy analysis as described above, to compositions along the line and demonstrating that no appropriate stationary points exist. The method of the present invention utilizes starting upper and lower pressures as search bounds, and then uses a half-interval technique to locate the thermodynamic miscibility pressure. A criterion is invoked by which the stepping procedure is replaced by the parallel displacement algorithm when the flash tieline extension is a certain distance from the unaltered feedstream composition for a given mechanism. Consequently, the method of the present invention employs the stepping procedure almost exclusively for pressures greater than the thermodynamic miscibility pressure, and a sequence of the stepping procedure coupled with a parallel displacement algorithm for pressures less than the thermodynamic miscibility pressure.

All computations in the following discussions of the examples have been performed using a generalized Redlich-Kwong Equation of State and a flash routine utilizing a minimum variable Newton-Raphson convergence algorithm. The thermodynamic miscibility pressure algorithm is not dependent upon these choices, but does require reliable flash convergence within two-phase regions. The timing information provided below reflects execution of these calculations on an IBM 3090 mainframe computer. The use of the Gibbs energy analysis to identify whether a mixture is or is not a stable single phase prior to attempting a two-phase flash calculation offers significant computational time savings. In terms of a single case, performing a flash calculation that results in a trivial, i.e., single phase, solution takes typically three (3) to ten (10) times longer than demonstrating that the mixture is a stable single phase. Even a converged two-phase flash calculation typically takes two (2) to three (3) times longer than a stationary point search in the Gibbs energy space. This disparity increases with the number of components. The time required to perform Gibbs energy analysis is necessarily additional to that needed for a flash calculation. However, the overall time savings offered by the use of Gibbs energy analysis when determining thermodynamic miscibility pressure has been determined to be typically 50% or sometimes greater.

The choice of the half-interval search for locating the thermodynamic minimum miscibility pressure is essentially a subjective one. There is no advantage in terms of computational time or convergence precision in attempting to restrict a search of the present method to one side of the thermodynamic miscibility pressure. Further computational time savings are gained by employing the parallel displacement algorithm in tandem with the stepping procedure as the means for identifying the existence and location of the coincident tieline.

EXAMPLE 1

Carbon Dioxide plus n-Butane plus n-Decane

The thermodynamic miscibility pressure was computed using a generalized Redlich-Kwong equation of state for the well-defined ternary mixture of fifty mol percent n-butane in n-decane (liquid phase) being contacted with 100% carbon dioxide (vapor phase) at 160° F. The equation of state parameters and component properties are given in Table 1. The thermodynamic miscibility pressure is achieved by the vaporizing mechanism with the results being displayed in Table 2. The CPU time listed is that used to perform both the Gibbs analysis (the stationary point searches) and the two-phase flash calculations. This CPU time makes up the majority of the overall run time of a computer program utilizing the method of the present invention. Use of the parallel displacement algorithm of the present invention with the stepping procedure reduces the number of computations significantly; e.g., there is a 28% decrease in the number of Gibbs tests and more importantly a 58% reduction in the number of two-phase flash calculations. Overall, 37% less computational time is required with the calculations that use the present invention.

Also listed is the precision with which the coincident tieline is found at those pressures where one exists (I). This precision is stated in terms of the perpendicular distance (d) in composition space between the unaltered feed composition and the extension of the last tieline located at the respectively pressure, defined as:

$$d = \sqrt{\sum_i (X_i - Z_i)^2}$$

where $X_i$ equals the composition for composition for component i on the extension of the tieline, and $Z_i$ equals the feed composition for component i.

The algoritnm of the present invention results in increased precision with less computational time and is responsible for the slightly lower (more precise) thermodynamic miscibility pressure calculated using it than that using the stepping procedure alone. It should be noted that in the two examples of the present invention some agreed upon tolerance of determining the minimum miscibility pressure is utilized; in most cases it is ±3 psi.

The reduction in computational time is attributable to the use of the parallel displacement algorithm and Gibbs energy analysis for computations at pressures below the thermodynamic minimum miscibility pressure, at which the stepping procedure executes many flash calculations in order to locate the coincident tieline and is attributable to the use of Gibbs energy analysis at pressures above the thermodynamic minimum miscibility pressure as well.

TABLE 1

Equation of State Parameters, Component Properties, and Fluid Compositions for the $CO_2 + nC_4 + nC_{10}$ System at 160° F.

| Component | $\Omega_a$ | $\Omega_b$ | $T_c$ °R | $p_c$ psia | MW | Liquid Comp. mol % | Gas Comp. mol % |
|---|---|---|---|---|---|---|---|
| $CO_2$ | 0.39883 | 0.07945 | 547.58 | 1070.74 | 44.009 | — | 100.00 |
| $nC_4$ | 0.42139 | 0.07973 | 765.29 | 550.56 | 58.124 | 50.00 | — |
| $nC_{10}$ | 0.46140 | 0.07216 | 1111.59 | 304.00 | 142.276 | 50.00 | — |

| Non-zero Binary Interaction Parameters | | |
|---|---|---|
| ij Component Pair | Cij | Dij |
| $CO_2$—$nC_4$ | 0.1614 | −0.0199 |
| $CO_2$—$nC_{10}$ | 0.1196 | −0.0135 |

TABLE 2

Comparison of Search Algorithms for the TMMP of a Well-Defined Ternary System

System: $CO_2$ + $n$-$C_4H_{10}$ + $n$-$C_{10}H_{22}$
Temperature = 160° F.
M = Miscible; I = Immiscible

| | Stepping Procedure | | | | Stepping Procedure With PDA | | | |
|---|---|---|---|---|---|---|---|---|
| | Number of | | | | Number of | | | |
| Pressure (psia) | Stationary Point Searches | Two-Phase Flashes | Distance d | CPU Time (sec) | Stationary Point Searches | Two-Phase Flashes | Distance d | CPU Time (sec) |
| 1800 (M) | 25 | 0 | — | 0.514 | 25 | 0 | — | 0.514 |
| 1500 (I) | 24 | 8 | $1.0 \times 10^{-4}$ | 0.497 | 22 | 7 | $1.1 \times 10^{-4}$ | 0.449 |
| 1650 (M) | 54 | 10(6)* | — | 1.434 | 66 | 15(5) | — | 1.764 |
| 1575 (I) | 28 | 12 | $7.1 \times 10^{-5}$ | 0.709 | 26 | 8 | $2.7 \times 10^{-5}$ | 0.539 |
| 1613 (I) | 77 | 41 | $1.2 \times 10^{-4}$ | 2.523 | 26 | 7 | $2.8 \times 10^{-7}$ | 0.590 |
| 1631 (M) | 59 | 19(9) | — | 2.184 | 57 | 5 | — | 1.228 |
| 1622 (M) | 72 | 34(5) | — | 2.564 | 41 | 13(2) | — | 1.928 |
| 1617 (I) | 80 | 43 | $1.9 \times 10^{-4}$ | 2.731 | 36 | 15(2) | $3.1 \times 10^{-7}$ | 1.106 |
| 1620 (I) | 82 | 44 | $1.7 \times 10^{-4}$ | 2.634 | 60 | 18(5) | — | 1.795 |
| TOTAL | 501 | 211(20) | | 15.790 | 359 | 88(14) | | 9.913 |

*(. . .) refers to the number of two-phase flashes resulting in trivial solutions.

EXAMPLE 2

Carbon Dioxide plus West Texas Reservoir Oil

For simulation of a system of carbon dioxide and West Texas reservoir oil, the $C_7+$ fraction of the oil was broken down into three (3) pseudocomponents having average carbon numbers of 7.8, 14.6, and 31.2, respectively. The fluid system overall included eleven (11) components, and the equation of state parameters and component properties used in these calculations are listed in Table 3. As is the case in the mixture set forth in Example 1, the use of Gibbs analysis and a parallel displacement algorithm provided a significant improvement in the terms of CPU time saved. For this particular description at 130° F., the vaporizing mechanism computed a minimum miscibility pressure of 2018 psia. Table 4 details the performance of the algorithm of the present invention at 2000 psia, illustrating the dramatically improved convergence that is achieved once the parallel displacement algorithm is invoked, after eight (8) iterations with the stepping procedure. Shown also in Table 4 is the density of the equilibrium liquid phase as a function of the number of two-phase flash calculations. For the stepping procedure used in concert with the parallel displacement algorithm, convergence is rapid once the parallel displacement algorithm is invoked. In this example, the parallel displacement algorithm is used once the distance d is less than 0.3, which is an arbitrary distance. The coincident tieline has a liquid density of 0.6055 g/cm3 and the convergence of the stepping procedure alone is very slow, requiring over forty five (45) steps to achieve the convergence of one parallel displacement algorithm step.

TABLE 3

Equation of State Parameters, Component Properties, and Fluid Compositions for the $CO_2$ + West Texas Reservoir Oil System at 130° F.

| Component | $\Omega_a$ | $\Omega_b$ | $T_c$ °R | $p_c$ psia | MW | Liquid Comp. mol % | Gas Comp. mol % |
|---|---|---|---|---|---|---|---|
| $C_1$ | 0.45176 | 0.08899 | 343.00 | 666.45 | 16.043 | 32.14 | — |
| $CO_2$ | 0.39870 | 0.07869 | 547.58 | 1070.74 | 44.009 | — | 100.00 |
| $C_2$ | 0.40867 | 0.08074 | 549.59 | 706.54 | 30.070 | 10.79 | — |
| $C_3$ | 0.41058 | 0.07914 | 665.73 | 616.04 | 44.097 | 14.43 | — |
| $nC_4$ | 0.42549 | 0.08026 | 765.29 | 550.56 | 58.124 | 7.87 | — |
| $iC_5$ | 0.43523 | 0.08112 | 828.69 | 483.00 | 72.146 | 0.90 | — |
| $nC_5$ | 0.43872 | 0.08042 | 845.19 | 489.50 | 72.146 | 2.05 | — |
| $C_6s$ | 0.44642 | 0.07919 | 913.79 | 440.00 | 86.172 | 1.17 | — |
| $C_{7-9}$ | 0.46019 | 0.07516 | 1038.18 | 381.98 | 118.634 | 15.74 | — |

TABLE 3-continued

Equation of State Parameters, Component Properties, and Fluid Compositions for the $CO_2$ + West Texas Reservoir Oil System at 130° F.

| | | | | | | | |
|---|---|---|---|---|---|---|---|
| $C_{10-24}$ | 0.47517 | 0.06533 | 1284.65 | 235.65 | 215.118 | 13.18 | — |
| $C_{25+}$ | 0.46493 | 0.05127 | 1580.72 | 105.06 | 429.620 | 1.73 | — |

Non-zero Binary Interaction Parameters

| ij Component Pair | Cij | Dij | ij Component Pair | Cij | Dij |
|---|---|---|---|---|---|
| $C_1$—$CO_2$ | 0.1755 | −0.0318 | $CO_2$—$C_2$ | 0.1654 | −0.0281 |
| $C_1$—$C_2$ | 0.0050 | — | $CO_2$—$C_3$ | 0.1594 | −0.0258 |
| $C_1$—$C_3$ | 0.0100 | — | $CO_2$—$nC_4$ | 0.1541 | −0.0239 |
| $C_1$—$nC_4$ | 0.0100 | — | $CO_2$—$iC_5$ | 0.1515 | −0.0229 |
| $C_1$—$iC_5$ | 0.0100 | — | $CO_2$—$nC_5$ | 0.1480 | −0.0216 |
| $C_1$—$nC_5$ | 0.0100 | — | $CO_2$—$C_{6S}$ | 0.1427 | −0.0196 |
| $C_1$—$C_{6S}$ | 0.0100 | — | $CO_2$—$C_{7-9}$ | 0.1298 | −0.0148 |
| $C_1$—$C_{7-9}$ | 0.0100 | — | $CO_2$—$C_{10-24}$ | 0.1028 | −0.0048 |
| $C_1$—$C_{10-24}$ | 0.0100 | — | $CO_2$—$C_{25+}$ | 0.0637 | 0.0098 |
| $C_1$—$C_{25+}$ | 0.0100 | — | | | |

TABLE 4

Comparison of Search Algorithms for the Location of a Coincident Tie Line at 2000 psia (About 18 psi Below the Computed TMMP) for an 11-Component Carbon Dioxide + West Texas Reservoir Oil System
Pressure = 2000 psia
Temperature = 130° F.

| | Stepping Procedure | | | Stepping Procedure with PDA | | |
|---|---|---|---|---|---|---|
| Flash Number | Liquid Density (g/cm³) | Distance d | Cumulative CPU Time (Sec) | Liquid Density (g/cm³) | Distance d | Cumulative CPU Time (Sec) |
| 1 | 0.6878 | 0.4530 | 0.515 | 0.6878 | 0.4530 | 0.515 |
| 2 | 0.6602 | 0.4924 | 0.672 | 0.6602 | 0.4924 | 0.672 |
| 3 | 0.6446 | 0.4883 | 0.819 | 0.6446 | 0.4883 | 0.819 |
| 5 | 0.6317 | 0.3309 | 1.056 | 0.6317 | 0.3309 | 1.056 |
| 7 | 0.6248 | 0.2939 | 1.426 | 0.6248 | 0.2939 | 1.426 |
| | | | | (PDA Invoked) | | |
| 9 | 0.6224 | 0.2603 | 1.565 | 0.6071 | $4.0 \times 10^{-2}$ | 1.557 |
| 10 | 0.6210 | 0.2404 | 1.837 | 0.6057 | $4.6 \times 10^{-3}$ | 1.673 |
| 11 | 0.6204 | 0.2313 | 2.169 | 0.6058 | $8.2 \times 10^{-4}$ | 1.809 |
| 12 | 0.6198 | 0.2226 | 2.254 | 0.6052 | $7.7 \times 10^{-4}$ | 1.935 |
| 13 | 0.6192 | 0.2141 | 2.338 | 0.6060 | $9.8 \times 10^{-4}$ | 2.062 |
| 14 | 0.6187 | 0.2059 | 2.420 | 0.6055 | $5.1 \times 10^{-5}$ | 2.189 |
| 15 | 0.6181 | 0.1980 | 2.504 | 0.6055 | $1.8 \times 10^{-5}$ | 2.316 |
| 25 | 0.6138 | 0.1333 | 3.325 | — | — | — |
| 35 | 0.6110 | 0.0891 | 4.101 | — | — | — |
| 45 | 0.6091 | 0.0592 | 4.839 | — | — | — |

Whereas the present invention has been described in particular relation to the drawings or to the examples made a part hereof and the drawings attached hereto, other and further modifications, apart from those shown or suggested herein, may be made within the scope and spirit of the present invention.

What is claimed is:

1. A method of determining the thermodynamic minimum miscibility pressure, of a three (3) or more component fluid system, encountered during displacement of an in-place fluid with an injected fluid comprising:
   (a) for a given initial pressure, varying the concentration of said injected fluid until a multiphase fluid state is indicated;
   (b) calculating coexisting equilibrium phase compositions for the multiphase fluid that define a tieline;
   (c) parallel translating the tieline, retaining the direction of its slope, to estimate a new tieline that is coincident with the in-place fluid's composition for a vaporizing mechanism or the injected fluid's composition for a condensing mechanism, the midpoint of which tieline is used to locate a multiphase state; and repeating b, c unit convergence;
   (d) performing steps a, b, c, utilizing an increased pressure if a coincident tieline is located, or utilizing a decreased pressure if a coincident tieline does not exist, until a boundary pressure is achieved representing the thermodynamic minimum miscibility pressure.

2. The method of claim 1 wherein step (a) comprises increasing the concentration of the injected fluid by a given increment, and performing a thermodynamic stability test to determine if a multiphase fluid state is present.

3. The method of claim 1 wherein step c comprises:
   (i) determining the slope of the tieline; and
   (ii) parallel translating the tieline, retaining the direction of its slope, to be coincicent with the in-place or injected fluid's composition.

4. The method of claim 3 wherein prior to step (c), the tieline is determined by a stepping procedure.

5. The method of claim 4 wherein the vaporizing mechanism is chosen in step (c) and wherein the stepping procedure for the vaporizing mechanism comprises:
  (i) for a given concentration of a first fluid (G) and a second fluid (L) determining an initial bubblepoint state $B_n$ where $G_n$ is the equilibrium vapor;
  (ii) determining a new bubblepoint state $B_{n+1}$ from a mixture of L and $G_n$; and
  (iii) repeating steps i and ii to approach a coincident tieline $\overline{bd}$ where $$b = \lim_{n \to \infty} B_n$$

$$d = \lim_{n \to \infty} G_n$$

6. The method of claim 4 wherein the condensing mechanism is chosen in step (c) and wherein the stepping procedure for the condensing mechanism comprises:
  (i) for a given concentration of a first fluid (G) and a second fluid (L) determining an initial dewpoint state $D_n$ wherein $L_n$ is the equilibrium liquid;
  (ii) determining a new dewpoint state $D_{n+1}$ from a mixture of $L_n$ and G; and
  (iii) repeating steps i and ii to approach a coincident tieline $\overline{bd}$ where $$b = \lim_{n \to \infty} L_n$$

$$d = \lim_{n \to \infty} D_n$$

7. The method of claim 1 wherein step (d) employs a first pressure and a second pressure that define a pressure range to be searched by:
  (i) attempting to locate a coincident tieline at a selected trial pressure within this search range and
  (ii) reducing the pressure range to be searched to that portion of the pressure range above the trial pressure if a coincident tieline is located or below the trial pressure if a coincident tieline does not exist.

8. The method of claim 1 wherein a first component is a liquid hydrocarbon.

9. The method of claim 8 wherein a second component is $CO_2$.

* * * * *